US007820249B2

(12) United States Patent
Nayar et al.

(10) Patent No.: US 7,820,249 B2
(45) Date of Patent: Oct. 26, 2010

(54) ULTRASONIC ENERGY SYSTEM AND METHOD INCLUDING A CERAMIC HORN

(75) Inventors: Satinder K. Nayar, Woodbury, MN (US); Ronald W. Gerdes, St. Paul, MN (US); Michael W. Carpenter, St. Paul, MN (US); Kamal E. Amin, Eagan, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 11/872,990

(22) Filed: Oct. 16, 2007

(65) Prior Publication Data

US 2008/0090024 A1 Apr. 17, 2008

Related U.S. Application Data

(62) Division of application No. 10/403,643, filed on Mar. 31, 2003, now Pat. No. 7,297,238.

(51) Int. Cl.
*B06B 1/20* (2006.01)
*B06B 1/00* (2006.01)
*B01J 19/10* (2006.01)
*A61L 2/00* (2006.01)

(52) U.S. Cl. .................... 427/601; 204/157.42; 422/20; 422/128

(58) Field of Classification Search ................. 427/601; 204/157.42; 422/20, 128
See application file for complete search history.

(56) References Cited

U.S. PATENT DOCUMENTS 3,636,859 A 1/1972 Null
3,645,504 A 2/1972 Jacke (Continued)

FOREIGN PATENT DOCUMENTS

EP 0 162 542 11/1985

(Continued)

OTHER PUBLICATIONS

Ohsawa, Y., et al., "Effects of Ultrasonic Vibration on Solidification Structures of Cast Iron", *Imono.*, vol. 67, No. 5, pp. 325-330 (1990).

(Continued)

*Primary Examiner*—Michael Cleveland
*Assistant Examiner*—Nathan H Empie
(74) *Attorney, Agent, or Firm*—Daniel R. Pastirik; James A. Baker

(57) ABSTRACT

An acoustic system for applying vibratory energy including a horn connected to an ultrasonic energy source. The horn defines an overall length and wavelength, and at least a leading section thereof is comprised of a ceramic material. The leading section has a length of at least ⅛ the horn wavelength. In one preferred embodiment, an entirety of the horn is a ceramic material, and is mounted to a separate component, such as a waveguide, via an interference fit. Regardless, by utilizing a ceramic material for at least a significant portion of the horn, the ultrasonic system of the present invention facilitates long-term operation in extreme environments such as high temperature and/or corrosive fluid mediums. The present invention is useful for fabrication of metal matrix composite wires.

3 Claims, 3 Drawing Sheets

U.S. PATENT DOCUMENTS

| | | | | | |
|---|---|---|---|---|---|
| 3,937,990 | A | | 2/1976 | Winston | |
| 4,647,336 | A | | 3/1987 | Coenen et al. | |
| 4,649,060 | A | | 3/1987 | Ishikawa et al. | |
| 4,948,409 | A | * | 8/1990 | Chenoweth et al. | 65/515 |
| 5,096,532 | A | | 3/1992 | Neuwirth et al. | |
| 5,529,816 | A | | 6/1996 | Sartini et al. | |
| 5,590,866 | A | | 1/1997 | Cunningham | |
| 5,603,444 | A | * | 2/1997 | Sato | 228/1.1 |
| 5,606,297 | A | | 2/1997 | Phillips | |
| 5,645,681 | A | | 7/1997 | Gopalakrishna et al. | |
| 5,707,483 | A | | 1/1998 | Nayar et al. | |
| 5,820,011 | A | | 10/1998 | Ito et al. | |
| 5,935,143 | A | | 8/1999 | Hood | |
| 5,945,642 | A | | 8/1999 | Nayar et al. | |
| 5,976,316 | A | * | 11/1999 | Mlinar et al. | 156/580.2 |
| 6,245,425 | B1 | | 6/2001 | McCullough et al. | |
| 6,329,056 | B1 | | 12/2001 | Deve et al. | |
| 6,344,270 | B1 | | 2/2002 | McCullough et al. | |
| 6,447,927 | B1 | | 9/2002 | McCullough et al. | |
| 6,498,421 | B1 | | 12/2002 | Oh et al. | |
| 6,652,992 | B1 | | 11/2003 | Gunnerman | |
| 6,786,383 | B2 | * | 9/2004 | Stegelmann | 228/1.1 |
| 7,297,238 | B2 | | 11/2007 | Nayar et al. | |

FOREIGN PATENT DOCUMENTS

| | | |
|---|---|---|
| JP | 61-34167 | 2/1986 |
| JP | 10-211589 | 8/1998 |
| WO | WO 00/71266 A1 | 11/2000 |

OTHER PUBLICATIONS

Zhou, G., et al., “The complex-mode vibration of ultrasonic vibration systems”, *Ultrasonics*, vol. 40, pp. 907-911 (2002).

* cited by examiner

ULTRASONIC ENERGY SYSTEM AND METHOD INCLUDING A CERAMIC HORN

CROSS REFERENCE TO RELATED APPLICATION

This application is a divisional of application Ser. No. 10/403,643 issued as U.S. Pat. No. 7,297,238, filed Mar. 31, 2003, which application is incorporated herein by reference.

BACKGROUND OF THE INVENTION

The present invention relates to acoustics. More particularly, it relates to an ultrasonic system and method incorporating a ceramic horn for long-term delivery of ultrasonic energy in harsh environments, such as high temperature and/or corrosive environments.

Ultrasonic is the science of the effects of sound vibrations beyond the limit of audible frequencies. The object of high-powered ultrasonic applications is to bring about some physical change in the material being treated. This process requires the flow of vibratory energy per unit of area or volume. Depending upon the application, the resulting power density may range from less than a watt to thousands of watts per square centimeter. In this regard, ultrasonics is used in a wide variety of applications, such as welding or cutting of materials.

Regardless of the specific application, the ultrasonic device or system itself generally consists of a transducer, a booster, a waveguide, and a horn. These components are often times referred to in combination as a "horn stack". The transducer converts electrical energy delivered by a power supply into high frequency mechanical vibration. The booster amplifies or adjusts the vibrational output from the transducer. The waveguide transfers the amplified vibration from the booster to the horn, and provides an appropriate surface for mounting of the horn. Notably, the waveguide component is normally employed for design purposes to reduce heat transfer to the transducer and to optimize performance of the horn stack in terms of acoustics and handling. However, the waveguide is not a required component and is not always employed. Instead, the horn is often times directly connected to the booster.

The horn is an acoustical tool usually having a length of a multiple of one-half of the horn material wavelength and is normally comprised, for example, of aluminum, titanium, or steel that transfers the mechanical vibratory energy to the desired application point. Horn displacement or amplitude is the peak-to-peak movement of the horn face. The ratio of horn output amplitude to the horn input amplitude is termed "gain". Gain is a function of the ratio of the mass of the horn at the vibration input and output sections. Generally, in horns, the direction of amplitude at the face of the horn is coincident with the direction of the applied mechanical vibrations.

Depending upon the particular application, the horn can assume a variety of shapes, including simple cylindrical, spool, bell, block, bar, etc. Further, the leading portion (or "tip") of the horn can have a size and/or shape differing form a remainder of the horn body. In certain configurations, the horn tip can be a replaceable component. As used throughout this specification, the term "horn" is inclusive of both uniformly shaped horns as well as horn structures that define an identifiable horn tip. Finally, for certain applications such as ultrasonic cutting and welding, an additional anvil component is provided. Regardless, however, ultrasonic horn configuration and material composition is relatively standard.

For most ultrasonic applications, accepted horn materials of aluminum, titanium, and steel are highly viable, with the primary material selection criteria being the desired operational frequency. The material to which the ultrasonic energy is applied is at room temperature and relatively inert, such that horn wear, if any, is minimal. However, with certain other ultrasonic applications, wear concerns may arise. In particular, where the horn operates in an intense environment (e.g., corrosive and/or high temperature), accepted horn materials may not provide acceptable results. For example, ultrasonic energy is commonly employed to effectuate infiltration of a fluid medium into a working part. Fabrication of fiber reinforced metal matrix composite wires are one such example whereby a tow of fibers are immersed in a molten metal (e.g., aluminum-based molten metal). Acoustic waves are introduced into the molten metal (via an ultrasonic horn immersed therein), causing the molten metal to infiltrate the fiber tow, thus producing the metal matrix composite wire. The molten aluminum represents an extremely harsh environment, as it is both intensely hot (on the order of 700° C.) and chemically corrosive. Under severe conditions, titanium and steel horns will quickly deteriorate. Other available metal-based horn constructions provide only nominal horn working life improvements. For example, metal matrix composite wire manufacturers commonly employ a series of niobium-molybdenum alloys (e.g., at least 4.5% molybdenum) for the horn. Even with this more rigorous material selection, niobium-based horns provide a limited working life in molten aluminum before re-machining is required. Moreover, near the end of their "first" life, niobium alloy horns become unstable, potentially creating unexpected processing problems. In addition, formation of the niobium-molybdenum alloy horns entails precise, lengthy and expensive casting, hot working, and final machining operations. In view of the high cost of these and other materials, niobium (and its alloys) and other accepted horn materials are less than optimal for harsh environment ultrasonic applications.

Ultrasonic devices are beneficially used in a number of applications. For certain implementations, however, the intense environment in which the ultrasonic horn operates renders current horn materials economically unavailing. Therefore, a need exists for an ultrasonic energy system, and in particular an ultrasonic horn, adapted to provide long-term performance under extreme operating conditions.

SUMMARY OF THE INVENTION

One aspect of the present invention relates to an acoustic system for applying vibratory energy, including a horn connected to an ultrasonic energy source. At least a leading section of the horn is comprised of a ceramic material. More particularly, the horn defines an overall length and wavelength. The ceramic material leading section has a length of at least ⅛ the horn wavelength. In one embodiment, an entirety of the horn is a ceramic material, and is mounted to a separate component, such as a waveguide, via an interference fit. Regardless, by utilizing a ceramic material for at least a leading section of the horn, the ultrasonic system of the present invention facilitates long-term operation in extreme environments such as high temperature and/or corrosive fluid mediums. For example, it has surprisingly been found that ceramic-based horns such as $SiN_4$, sialon, $Al_2O_3$, SiC, $TiB_2$, etc., have virtually no chemical reactivity when applying vibratory energy to highly corrosive and molten metal media, especially molten aluminum.

Another aspect of the present invention relates to a method of applying ultrasonic energy in a fluid medium, and includes providing the fluid medium, and connecting an ultrasonic energy source to a horn at least a leading ⅛ wavelength of which is a ceramic material. At least a portion of the horn is immersed in the fluid medium. To this end, the horn is configured such that an entirety of the immersed portion thereof is comprised of the ceramic material. Finally, the ultrasonic energy source is operated such that the horn delivers ultrasonic energy to the fluid medium. In one embodiment, the fluid medium is corrosive and has a temperature of at least 500° C., and the method is characterized by not replacing the horn for at least 100 hours of ultrasonic energy delivery.

Yet another aspect of the present invention relates to a method of making a continuous composite wire. The method includes providing a contained volume of molten metal matrix material having a temperature of at least 600° C. A tow comprising a plurality of substantially continuous fibers is immersed into the contained volume of molten metal matrix material. Ultrasonic energy is imparted via a horn, at least the leading ⅛ wavelength of which is ceramic. The so-imparted ultrasonic energy causes vibration of at least a portion of the contained volume of molten metal matrix material to permit at least a portion of the molten metal matrix material to infiltrate into the plurality of fibers such that an infiltrated plurality of fibers is provided. Finally, the infiltrated plurality of fibers is withdrawn from the contained volume of molten metal matrix material.

DETAILED DESCRIPTION OF THE PREFERRED EMBODIMENTS

Figure 1:
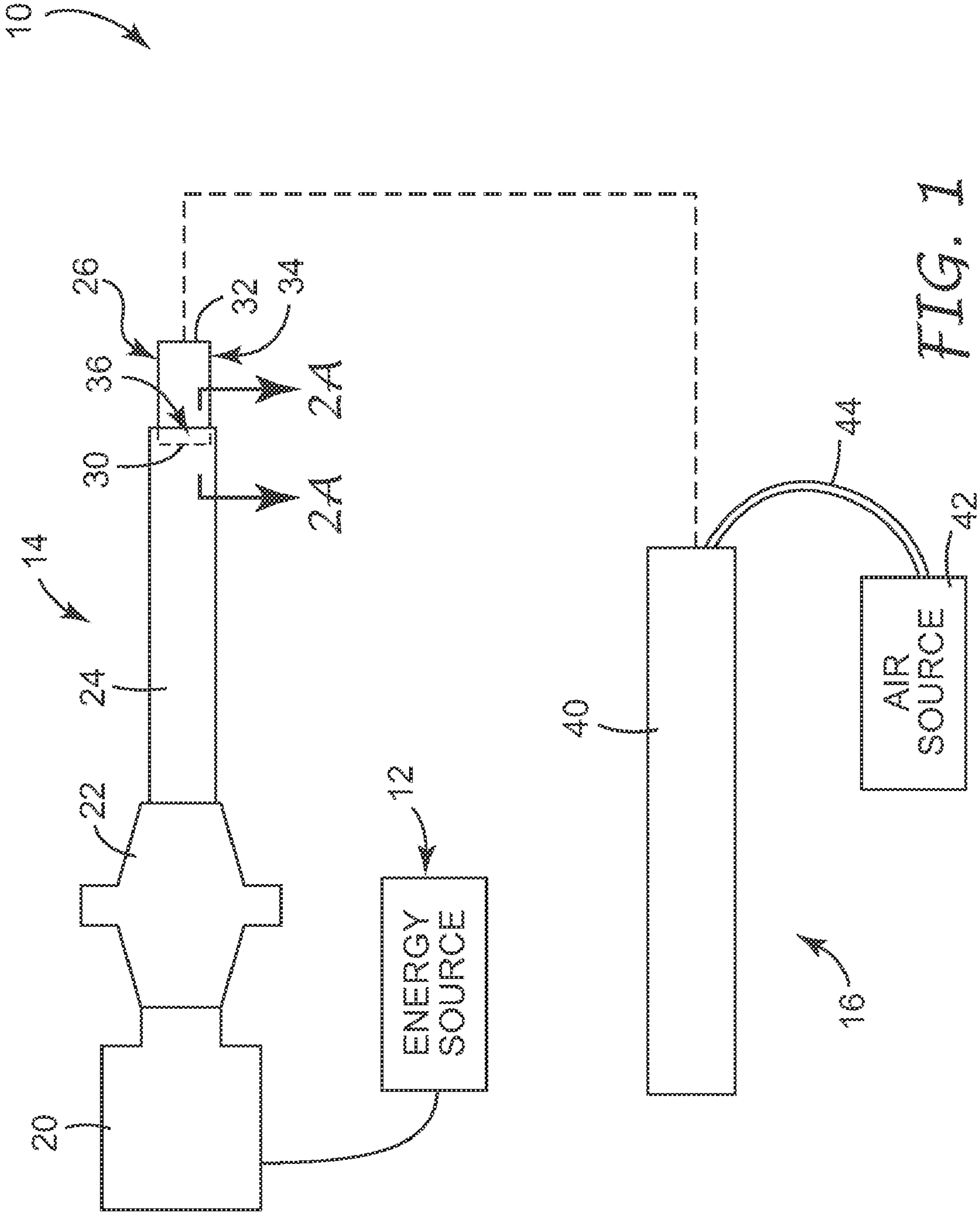
FIG. 1 is an exploded view of an ultrasonic energy system in accordance with the present invention, with portions being shown in block form.

One embodiment of an ultrasonic system 10 in accordance with the present invention is provided in FIG. 1. In general terms, the ultrasonic system 10 includes an energy source 12 (shown in block form), an ultrasonic or horn stack 14, and a cooling system 16. Details on the various components are described below. In general terms, however, the horn stack 14 includes a transducer 20, a booster 22, a waveguide 24, and a horn 26. At least a portion of the horn 26 is comprised of a ceramic material and is adapted to deliver mechanical vibratory energy generated by the transducer 20, the booster 22, and the waveguide 24 via input from the energy source 12. The cooling system 16, as described below, cools an interface between the horn 26 and the waveguide 24. With this configuration, the ultrasonic system 10, and in particular the horn 26, can provide ultrasonic energy in extreme operating environments (e.g., elevated temperature and/or chemically corrosive) on a long-term basis.

Several components of the ultrasonic system 10 are of types known in the art. For example, the energy source 12, the transducer 20, and the booster 22 are generally conventional components, and can assume a variety of forms. For example, in one embodiment, the energy source 12 is configured to provide high frequency electrical energy to the transducer 20. The transducer 20 converts electricity from the energy source 12 to mechanical vibration, nominally 20 kHz. The transducer 20 in accordance with the present invention can thus be any available type such as piezoelectric, electromechanical, etc. Finally, the booster 22 is also of a type known in the art, adapted to amplify the vibrational output from the transducer 20 and transfer the same to waveguide 24 horn 26. In this regard, while the system 10 can include the waveguide 24 between the booster 22 and the horn 26, in an alternative embodiment, the horn 26 is directly connected to the booster 22 such that the waveguide 24 is eliminated.

Unlike the components described above, the horn 26, and where provided the waveguide 24, represent distinct improvements over known ultrasonic systems. In particular, a substantial portion of the horn 26, and in one embodiment an entirety of the horn 26, is formed of a ceramic material. By way of reference, the horn 26 is defined by a trailing end 30 and a leading end 32. The trailing end 30 is attached to the waveguide 24, whereas the leading end 32 represents the working end of the horn 26. Thus, for example, where the ultrasonic system 10 is employed to deliver ultrasonic energy to a fluid medium, the leading end 32 (along with portions of the horn 26 adjacent the leading end 32), is immersed in the fluid medium. With these designations in mind, the horn 26 is defined by a length from the trailing end 30 to the leading end 32, and defines a horn material wavelength. The ceramic portion of the horn 26 is at least ⅛ of this wavelength in length, extending proximally from the leading end 32 toward the trailing end 30. In other words, the horn 26 defines a ceramic leading section 34 having a length of at least ⅛ the horn material wavelength. Alternatively, the ceramic portion leading section 34 can have a length that is greater than ⅛ the horn material wavelength, for example at least ¼ wavelength or ½ wavelength. In a most preferred embodiment, an entirety of the horn 26 is formed of a ceramic material. Regardless, the ceramic portion of the horn is not a mere coating or small head piece; instead, the present invention utilizes ceramic along a significant portion of the horn 26.

A variety of ceramic materials are acceptable for the horn 26 (or the leading section 34 thereof as previously described), and includes at least one of carbide, nitride, and/or oxide materials. For example, the ceramic portion of the horn 26 can be silicon nitride, aluminum oxide, titanium diboride, zirconia, silicon carbide, etc. In an even more preferred embodiment, the ceramic portion of the horn 26 is an alumina, silicon nitride ceramic composite, such as sialon ($Si_{6-x}Al_xO_xN_{8-x}$).

While the horn 26 is depicted in FIG. 1 as being a cylindrical rod, other shapes are available. For example, the horn 26 can be a rectangular- or square-shaped (in cross-section) bar, spherical, tapered, double tapered, etc. The selected shape of the horn 26 is a function of the intended end application.

Depending upon how the horn 26 is provided, the waveguide 24 can assume a variety of forms, as can the coupling therebetween. For example, where a trailing section 36 of the horn 26 is something other than ceramic (e.g., titanium, niobium, or other conventional horn material), the waveguide 24 can also be of a known configuration, as can the technique by which the horn 26 is secured to the waveguide 24. For example, where the trailing section 36 of the horn 26 is comprised of a standard horn material, such as niobium and its alloys, the waveguide 24 can be formed of a titanium and/or steel material, and the horn 26 mounted thereto with a threaded fastener. Alternative mounting techniques not previously employed in the ultrasonic horn art are described below.

Figure 2A:
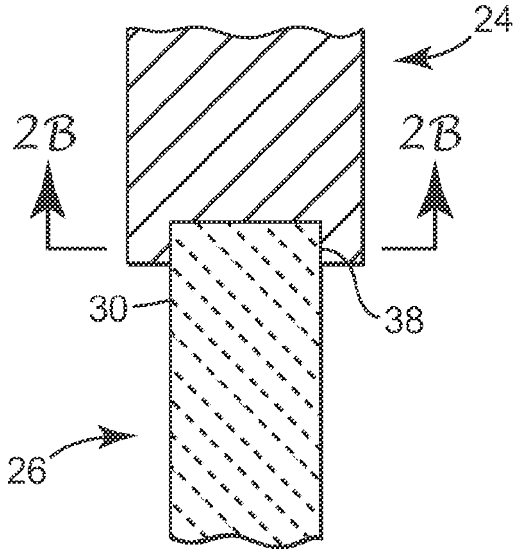
FIG. 2A is an enlarged, cross-sectional view of a portion of the ultrasonic system of FIG. 1.
Figure 2B:
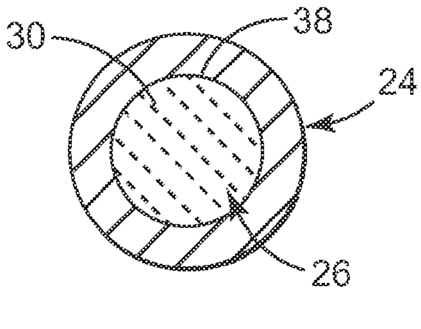
FIG. 2B is a cross-sectional view of a portion of FIG. 2A along the lines 2B-2B.

In accordance with one embodiment in which an entirety of the horn 26 is formed of a ceramic material, a mechanical fit mounting technique can be employed to couple the horn 26 and the waveguide 24 (or the booster 22 when the waveguide 24 not included). For example, and with reference with FIGS. 2A and 2B, the waveguide 24 and the horn 26 are adapted to facilitate an interference fit therebetween. More particularly, the waveguide 24 forms an internal bore 38 having a dimension(s) corresponding with an outer dimension(s) of the horn 26. Thus, for example, where the horn 26 is provided as a cylindrical rod, the bore 38 and the trailing end 30 define diameters selected to generate an appropriate interference fit therebetween. In this regard, and as previously described, the ultrasonic system 10 is preferably adapted for use in high temperature environments (i.e., at least 200° C.; at least 350° C. in another embodiment; at least 500° C. in another embodiment), such as molten metal. Under these conditions, the interference or junction fit must be such that the ceramic horn 26 does not loosen relative to the waveguide 24 at the high temperatures likely encountered. The waveguide 24 is formed in one embodiment of a material other than ceramic to best facilitate connection between the booster 22 and the horn 26; it being recognized that by using varying materials for the waveguide 24 and the horn 26, these components will expand at different rates when subjected to highly elevated temperatures. In conjunction with this material expansion, hoop stresses will be imparted by the horn 26 onto the waveguide 24 as the horn 26 expands. With this in mind, and in one embodiment, the waveguide 24 is formed of a titanium material as opposed to other often employed materials for these high temperature applications (such as niobium) because the hoop stresses caused by the interference fit are much less than the yield strength of titanium. That is to say, niobium (and alloys thereof) is unable to withstand expected hoop stresses at elevated temperatures (e.g., on the order of at least 500° C.). For example, where the ultrasonic system 10 is used to apply ultrasonic energy to a molten metal medium, the waveguide 24 is preferably titanium, and the bore 40 is selected to provide an interference fit of 0.003 inch at room temperature.

The above interference fit clamping-type technique for assembling the horn 26 to the waveguide 24 is but one acceptable approach. Other mechanical clamping techniques can be employed, such as forming the waveguide 24 to include a split clamp configuration, etc. Regardless, the junction point between the waveguide 24 and the horn 26 is preferably at the anti-node of the waveguide 24, although other junction points (e.g., a vibrational node of the waveguide 24) are acceptable. Regardless, the interference assembly technique of the horn 26 to the waveguide 24 facilitates overall tuning of the horn stack 14 by machining or adjusting of the waveguide 24. This is in contrast to accepted techniques whereby the horn 26 is precisely machined as a half-wavelength horn. Due to the potential complications associated with machining of ceramics, the present invention facilitating machining the waveguide 24 as part of the tuning process. As such, the horn 26 can have a length that is something other than a half-wavelength. To this end, it is recognized that typically a half-wavelength requirement is needed for both the waveguide 24 and the horn 26 lengths to maintain nodes at a mid-span of the waveguide 24/horn 26, and anti-nodes at the waveguide 24/horn 26 interface(s) for optimal resonance (e.g., 20 kHz) with minimum consumption of energy throughout the horn stack 14.

Figure 3:
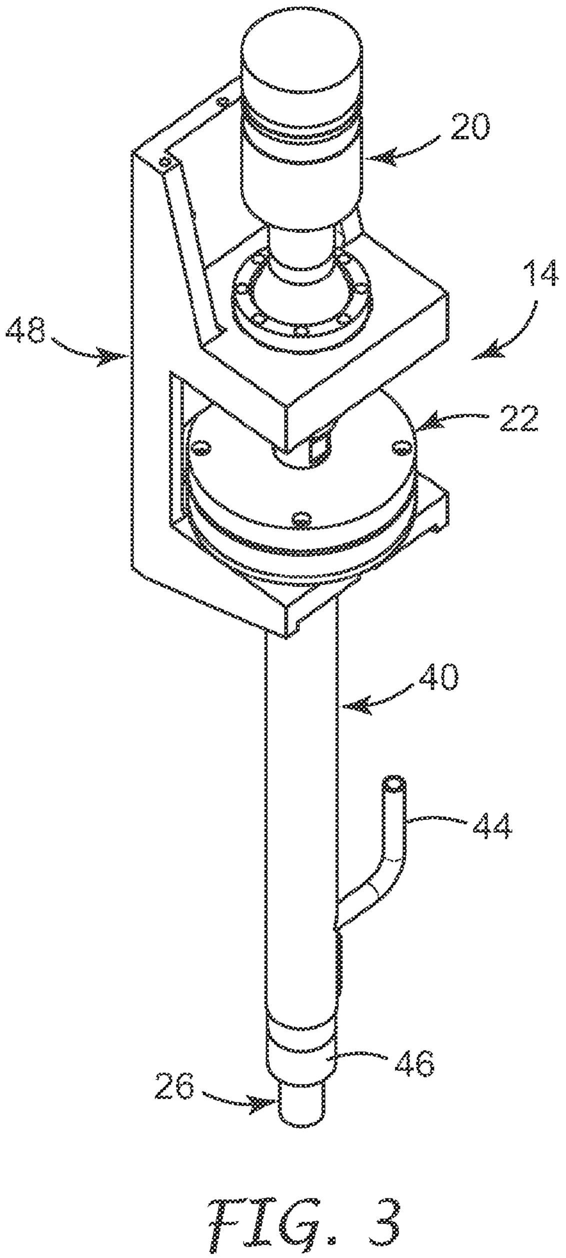
FIG. 3 is a perspective view of the ultrasonic horn stack of FIG. 1 upon final assembly.

Returning to FIG. 1, the ultrasonic system 10 includes, in one embodiment, the cooling system 16 for effectuating cooling of the previously described junction between the horn 26 and the waveguide 24, as well as other components of the horn stack 14. In general terms, one embodiment of the cooling system 16 includes a shroud 40, an air source 42, and a conduit(s) 44. With additional reference to FIG. 3, the shroud 40 is sized for placement about the horn stack 14, with a distal end 46 thereof being positioned adjacent the waveguide 24/horn 26 junction. The conduit 44 fluidly connects the air source 42 with an interior of the shroud 40, thereby directing forced airflow from the air source 42 within the shroud 40. In one embodiment, the system 10 further includes a bracket 48 for mounting of the horn stack 14.

Figure 4:
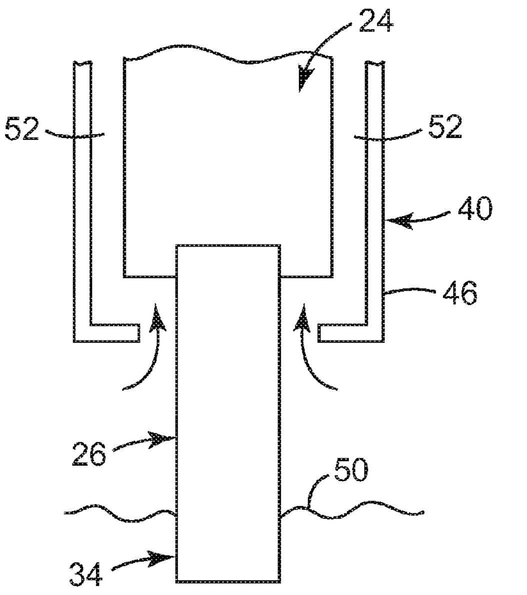
FIG. 4 is an enlarged, schematic illustration of a portion of the ultrasonic system of FIG. 1 during use.

As best shown in FIG. 4, for example, during use, a portion of the horn 26 (and in particular at least a portion of the ceramic leading section 34) is immersed within a fluid medium 50. For certain applications, the fluid medium 50 can be extremely hot, such as molten aluminum having a temperature of approximately 710° C. Under these conditions, heat from the fluid medium 50 may negatively affect stability of the mounting between the waveguide 24 and the horn 26. In accordance with one embodiment, however, the cooling system 16 minimizes potential complications. In particular, the shroud 40 surrounds the waveguide 24/horn 26 junction, and defines a gap 52 between the shroud 40 and the waveguide 24/horn 26. Air from the air source 42 (FIG. 1) is forced into this gap 52 via the conduit 44 (FIG. 1) and passes outwardly from the shroud 40. Thus, the forced airflow removes heat from the waveguide 24/horn 26 junction, and cools the waveguide 24, the booster 22 (FIG. 1) and the transducer 20 (FIG. 2). Alternatively, other cooling system designs can be employed. Further, where heat from the fluid medium 50 is of less concern and/or the waveguide 24/horn 26 assembly is stable at expected temperatures, the cooling system 16 can be eliminated entirely.

The ultrasonic system 10 of the present invention is highly useful for a variety of ultrasonic applications, especially those involving extreme environments, such as corrosive environments, high temperature fluid mediums, combinations thereof In particular, by forming a relevant portion of the horn 26, preferably an entirety of horn 26, of a ceramic material, the horn 26 will not rapidly erode upon exposure to the extreme environment. In particular, selected ceramic materials, such as sialon, silicon nitride, titanium diboride, silicon carbide, aluminum oxide, etc., are highly stable at elevated temperatures, and generally will not corrode when exposed to acidic fluids such as molten aluminum. Further, with respect to high temperature applications, the preferred ceramic horn 26 exhibits reduced heat transfer characteristics (as compared to known high temperature application horn materials such a niobium and niobium-molybdenum alloys) from the high temperature medium to a remainder of the horn stack. Thus, for molten metal applications having temperatures in excess of 700° C., the preferred ceramic horn 26 minimizes heat transfer to the transducer 20, thereby greatly reducing the opportunity for damage to the transducer crystal. Where the horn 26 is entirely ceramic, the horn 26 exhibits virtually constant stiffness and density characteristics at ambient and elevated temperatures (e.g., in the range of 700° C.).

Figure 5:
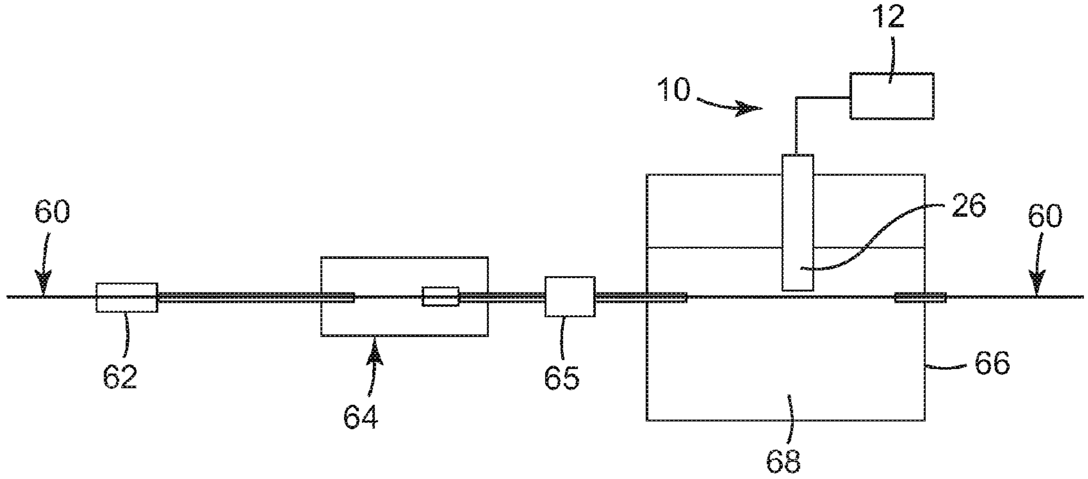
FIG. 5 is a schematic illustration of an apparatus for producing composite metal matrix wires using ultrasonic energy in accordance with the present invention.

With the above in mind, one exemplary application of the ultrasonic system 10 in accordance with the present invention is in the fabrication of fiber reinforced aluminum matrix composite wires. FIG. 5 schematically illustrates one example of a metal matrix composite wire fabrication system employing the ultrasonic system 10 in accordance with the present invention. The fabrication method reflected in FIG. 5 is referred to as "cast through" and begins with a tow of polycrystalline $\alpha$-$Al_2O_3$ fiber 60 transported through an inlet die 62 and into a vacuum chamber 64 where the tow 60 is evacuated. The tow 60 is then transported through a cooling fixture 65 and then to a vessel 66 containing a metal matrix 68 in molten form. In general terms, the molten matrix metal 68 may be aluminum-based, having a temperature of at least 600° C., typically approximately 700° C. While immersed in the molten matrix metal 68, the tow 60 is subjected to ultrasonic energy provided by the ultrasonic system 10, and in particular the horn 26 that is otherwise immersed in the molten metal matrix 68. Once again, an entirety of the horn 26 is preferably ceramic. Alternatively, where only the leading section 34 (FIG. 1) is ceramic, the immersed portion of the horn 26 consists only of the ceramic leading section 34 (or a portion thereof). Regardless, the horn 26 vibrates the molten metal matrix 68, preferably at 20 kHz. In doing so, the matrix material is caused to thoroughly infiltrate the fiber tow 60. The infiltrated fiber tow 60 is drawn from the molten metal matrix 68. A number of other metal matrix composite wire fabrication techniques in which the system 10 of the present invention is useful are known, one of which is described, for example, in U.S. Pat. No. 6,245,425, the teachings of which are incorporated herein by reference.

Regardless of the exact fabrication technique, and unlike existing ultrasonic systems incorporating a niobium horn, the ultrasonic system 10 of the present invention provides an extended operational time period without requiring replacement of the horn 26. That is to say, niobium horns (and niobium alloys) used in molten metal infiltration applications typically fail due to erosion in less than 50 working hours. In contrast, the ultrasonic system 10, and in particular the horn 26, in accordance with the present invention surprisingly exhibits a useful working life well in excess of 100 working hours in molten metal; even in excess of 200 working hours in molten metal.

While the ultrasonic system 10 has been described as preferably being used with the fabrication of fiber reinforced aluminum matrix composite wire, benefits will be recognized with other acoustic or ultrasonic applications. Thus, the present invention is in no way limited to any one particular acoustic or ultrasonic application.

EXAMPLES

Objects and advantages of this invention are further illustrated by the following examples, the particular materials and amounts thereof recited in these examples, as well as other conditions and details, should not be construed to unduly limit this invention.

Example 1

An ultrasonic horn stack was prepared by forming a cylindrical rod sialon horn having a length of approximately 11.75 inches and a diameter of 1 inch. The horn was interference fit-mounted to a titanium waveguide. The waveguide was mounted to a booster that in turn was mounted to a transducer. An appropriate energy source was electrically connected to the transducer. The so-constructed ultrasonic system was then operated to apply ultrasonic energy to a molten aluminum bath. In particular, aluminum metal was heated to a temperature in the range of about 705° C.-715° C. to form the molten aluminum bath. The ceramic horn was partially immersed in the molten aluminum bath, and the horn stack operated such that the horn transmitted approximately 65 watts at approximately 20 kHz and subjected to air cooling. At approximately 50-hour intervals, the horn was removed from the molten aluminum bath, acid etched, and visually checked for erosion. Further, stability of the junction between the waveguide and the horn was reviewed. The power and frequency readings, along with erosion and junction stability characteristics are noted in Table 1 below. After 200 hours of operation, the waveguide/horn junction remained highly stable, and very limited horn erosion or fatigue was identified. Thus, the ceramic horn was able to withstand delivery of ultrasonic energy to a corrosive, high temperature environment for an extended period of time. Notably, it is believed that horn and waveguide/horn junction stability would have been maintained for many additional hours beyond the 200-hour test. Additionally, measurements were taken to determine whether slight erosion of the ceramic horn results in transfer of horn material, and in particular silicon, to the molten bath. With respect to Example 1, the silicon content of the molten aluminum bath was measured at 153 ppm prior to applying ultrasonic energy. After 150 hours, the silicon content of the bath was again tested, and was found to be 135 ppm. Thus, silicon content of the bath was not adversely affected by the ceramic ultrasonic horn.

TABLE 1

| Hours | Power (watts) | Frequency (kHz) | Horn Erosion | Junction Stability |
|---|---|---|---|---|
| 54 | 64 | 19,670 | None | Highly stable |
| 100 | 64 | 19,636 | None | Highly stable |
| 150 | 68 | 19,636 | Slight | Highly stable |
| 200 | 69 | 19,670 | Slight | Highly stable |

Example 2

Preparation of Metal Matrix Composite Wires.

Composite metal matrix wires were prepared using tows of NEXTEL™ 610 alumina ceramic fibers (commercially available from 3M Company, St. Paul, Minn.) immersed in a molten aluminum-based bath and subjected to ultrasonic energy to effectuate infiltration of the tow. In particular, an ultrasonic system that included a sialon horn, similar to the horn described in Example 1, was employed as part of a cast through methodology, shown schematically in FIG. 5. The process parameters were similar to those employed for fabricating aluminum matrix composites (AMC) and fully described in Example 1 of U.S. Pat. No. 6,344,270 ('270), herein incorporated by reference. The sialon horn of present invention replaced the niobium alloy horn described in the '270 patent. With this Example, the sialon horn transmitted about 65 watts at a frequency of about 20 kHz. Approximately 6,500 feet of wire was produced over the course of thirteen experimental runs, and was tensile tested using a tensile tester (commercially available as Instron 4201 tester from Instron of Canton, Mass.), pursuant to ASTM D 3379-75 (Standard Test Methods for Tensile Strength and Young's Modulus for High Modulus Single-Filament Materials). The tensile strength of the wires produced in accordance with Example 2 was virtually identical to that associated with metal matrix composite wires fabricated using a niobium-alloy ultrasonic horn, exhibiting a longitudinal strength in the range of approximately 1.51 GPa.

Although the present invention has been described with reference to preferred embodiments, workers skilled in the art will recognize that changes can be made in form and detail without departing from the spirit and scope of the present invention.

What is claimed is:

1. A method of making a continuous composite wire, the method comprising:

providing a contained volume of molten metal matrix material having a temperature of at least 600° C.;

immersing at least one tow comprising a plurality of substantially continuous fibers into the contained volume of molten metal matrix material;

imparting ultrasonic energy with a horn connected to an ultrasonic energy source to cause vibration of at least a portion of the contained volume of molten metal matrix material to permit at least a portion of the molten metal matrix material to infiltrate into the plurality of fibers such that an infiltrated plurality of fibers is provided, wherein the horn is ceramic, wherein the horn is defined by a trailing end and a leading end further defining a horn length extending there-between, wherein the horn length is other than one half a wavelength of the ultrasonic energy source, and further wherein the ultrasonic energy source includes a titanium mounting component consisting of a waveguide for securing the trailing end of the horn in an interference fit with the mounting component such that a junction point between the waveguide and the trailing end of the horn is at a vibrational node of the waveguide, the horn being secured to the mounting component by hoop stresses in the titanium mounting component produced at the temperature of the molten metal matrix material; and withdrawing the infiltrated plurality of fibers from the contained volume of molten metal matrix material.

2. The method of claim 1, wherein the horn is a cylindrical rod, and further wherein the mounting component defines a circular bore, wherein the trailing end of the horn is received within the circular bore to provide an interference fit of 0.003 inch at room temperature.

3. The method of claim 1, wherein continuous composite wires are fabricated for at least 100 hours without replacing the horn.

* * * * *